(12) United States Patent
Thompson et al.

(10) Patent No.: US 6,539,253 B2
(45) Date of Patent: Mar. 25, 2003

(54) IMPLANTABLE MEDICAL DEVICE INCORPORATING INTEGRATED CIRCUIT NOTCH FILTERS

(75) Inventors: David L. Thompson, Fridley, MN (US); Gregory J. Haubrich, Champlin, MN (US); Steven D. Goedeke, Forest Lake, MN (US)

(73) Assignee: Medtronic, Inc., Minneapolis, MN (US)

(*) Notice: Subject to any disclaimer, the term of this patent is extended or adjusted under 35 U.S.C. 154(b) by 45 days.

(21) Appl. No.: 09/729,845

(22) Filed: Dec. 5, 2000

(65) Prior Publication Data

US 2002/0026224 A1 Feb. 28, 2002

Related U.S. Application Data

(63) Continuation-in-part of application No. 09/648,604, filed on Aug. 26, 2000.

(51) Int. Cl.⁷ .................................................. A61N 1/16
(52) U.S. Cl. ............................................. 607/2; 607/60
(58) Field of Search ................................ 607/2, 9, 60, 5

(56) References Cited

U.S. PATENT DOCUMENTS

| | | | |
|---|---|---|---|
| 4,254,775 A | 3/1981 | Langer | 607/5 |
| 4,357,943 A | 11/1982 | Thompson et al. | 128/419 PG |
| 4,390,020 A | 6/1983 | Herpers | 128/419 PG |
| 4,401,119 A | 8/1983 | Herpers | 128/419 PG |
| 4,436,093 A | 3/1984 | Belt | 128/419 PG |
| 4,596,252 A | 6/1986 | Nelson | 128/419 PG |
| 4,681,111 A | 7/1987 | Silvian | 607/59 |
| 5,188,117 A | 2/1993 | Steinhaus et al. | 128/708 |
| 5,265,588 A | 11/1993 | Nelson et al. | 607/5 |
| 5,331,966 A | 7/1994 | Bennett et al. | 600/508 |
| 5,342,408 A | 8/1994 | deCoriolis et al. | 607/32 |

(List continued on next page.)

FOREIGN PATENT DOCUMENTS

WO WO 98/02209 1/1998 .......... A61N/1/375

OTHER PUBLICATIONS

"Micromachined Planar Spiral Inductor in Standard GaAs HEMT MMIC Technology", Ribas, et al., *IEEE Electron Device Letters*, vol. 19, No. 8, Aug. 1998, pp. 285–287.

(List continued on next page.)

Primary Examiner—Carl Layno
(74) Attorney, Agent, or Firm—Girma Wolde-Michael

(57) ABSTRACT

Implantable medical devices (IMDs) having sense amplifiers for sensing physiologic signals and parameters, RF telemetry capabilities for uplink transmitting patient data and downlink receiving programming and interrogation commands to and from an external programmer or other medical device are disclosed. At least one IC chip and discrete components have a volume and dimensions that are optimally minimized to reduce its volumetric form factor. Miniaturization techniques include forming notch filters of MEMS structures or forming discrete circuit notch filters by one or more of: (1) IC fabricating inductors into one or more IC chips mounted to the RF module substrate; (2) mounting each IC chip into a well of the RF module substrate and using short bonding wires to electrically connect bond pads of the RF module substrate and the IC chip; and (3) surface mounting discrete capacitors over IC chips to reduce space taken up on the RF module substrate. The IC fabricated inductors are preferably fabricated as planar spiral wound conductive traces formed of high conductive metals to reduce trace height and width while maintaining low resistance, thereby reducing parasitic capacitances between adjacent trace side walls and with a ground plane of the IC chip. The spiral winding preferably is square or rectangular, but having truncated turns to eliminate 90° angles that cause point-to-point parasitic capacitances. The planar spiral wound conductive traces are further preferably suspended over the ground plane of the IC chip substrate by micromachining underlying substrate material away to thereby reduce parasitic capacitances.

38 Claims, 6 Drawing Sheets

U.S. PATENT DOCUMENTS

| | | | |
|---|---|---|---|
| 5,416,356 A | 5/1995 | Staudinger et al. | 257/531 |
| 5,425,373 A | 6/1995 | Cuasey, III | 600/510 |
| 5,455,547 A | 10/1995 | Lin et al. | 333/186 |
| 5,491,604 A | 2/1996 | Nguyen et al. | 361/278 |
| 5,535,752 A | 7/1996 | Halperin et al. | 128/670 |
| 5,537,083 A | 7/1996 | Lin et al. | 333/186 |
| 5,564,434 A | 10/1996 | Halperin et al. | 128/748 |
| 5,589,082 A | 12/1996 | Lin et al. | 216/2 |
| 5,626,620 A | 5/1997 | Kieval et al. | 607/9 |
| 5,697,958 A | 12/1997 | Paul et al. | 607/31 |
| 5,767,791 A | 6/1998 | Stoop et al. | 340/870.11 |
| 5,793,272 A | 8/1998 | Burghartz et al. | 336/200 |
| 5,836,992 A | 11/1998 | Thompson et al. | 607/36 |
| 5,839,062 A | 11/1998 | Nguyen et al. | 455/323 |
| 5,843,139 A | 12/1998 | Goedeke et al. | 607/32 |
| 5,861,019 A | 1/1999 | Sun et al. | 607/60 |
| 5,872,489 A | 2/1999 | Chang et al. | 331/179 |
| 5,884,990 A | 3/1999 | Burghartz et al. | 336/200 |
| 5,931,857 A | 8/1999 | Prieve et al. | 607/14 |
| 5,944,659 A | 8/1999 | Flach et al. | 600/300 |
| 5,978,710 A | 11/1999 | Prutchi et al. | 607/17 |
| 6,054,329 A | 4/2000 | Burghartz et al. | 438/3 |
| 6,114,937 A | 9/2000 | Burghartz et al. | 336/200 |

OTHER PUBLICATIONS

"Analysis, Design, and Optimization of Spiral Inductors and Transformers for Si RF IC's", Niknejad, et al., *IEEE Journal of Solid–State Circuits*, vol. 33, No. 10, Oct. 1998, pp. 1470–1481.

"A Novel High–Q and Wide–Frequency–Range Using Si 3–D MMIC Technology", Kamogawa, et al, *IEEE Microwave and Guided Wave Letters*, vol. 9, No. 1, Jan. 1999, pp. 16–18.

"Integrated Circuit Technology Options for RFIC's—Present Status and Future Directions", Larson, *IEEE Journal of Solid–State Circuits*, vol. 33, No. 3, Mar. 1998, pp. 387–399.

"Micromachined Electro–Mechanically Tunable Capacitors and Their Applications to RF IC's", Dec et al., *IEEE Transactions on Microwave Theory and Techniques*, vol. 46, No. 12, Dec. 1998, pp. 2587–2595.

"RF Circuit design Aspects of Spiral Inductors on Silicon", Burghartz, et al., *IEEE Journal of Solid–State Circuits*, vol. 33, No. 12, Dec., 1998, pp. 2028–2034.

"Suspended SOI Structure for Advanced 0.1 $\mu$m CMOS RF Devices", Hisamoto, et al., *IEEE Transactions on Electron Devices*, vol. 45, No. 5, May 1998, pp. 1039–1046.

"Influence of D–Net (European GSM–Standard) Cellular Phones on Pacemaker Function in 50 Patients with Permanent Pacemakers", Wilke et al., *PACE*, vol. 19, pp. 1456–1458, 10/96.

"Pacemaker Inhibition and Asystole in a Pacemaker Dependent Patient", Yesil et al. (*PACE*, vol. 18, p. 1963, Oct. 1995).

IMPLANTABLE MEDICAL DEVICE INCORPORATING INTEGRATED CIRCUIT NOTCH FILTERS

This application is a continuation-in-part of co-pending, commonly assigned U.S. patent application Ser. No. 09/648,604 filed Aug. 26, 2000, in the names of G. Haubrich et al. for IMPLANTED MEDICAL DEVICE TELEMETRY USING INTEGRATED MICROELECTROMECHANICAL FILTERING.

FIELD OF THE INVENTION

This invention relates generally to implantable medical devices (IMDs) having sense amplifiers for sensing physiologic signals and parameters, RF telemetry capabilities for uplink transmitting patient data and downlink receiving programming and interrogation commands to and from an external programmer or other medical device, and other electronic circuitry susceptible to electromagnetic interference (EMI), and more particularly to miniaturized, integrated circuit notch filters for use in such circuitry to reject EMI.

BACKGROUND OF THE INVENTION

A wide variety of IMDs that employ electronic circuitry for providing electrical stimulation of body tissue and/or monitoring a physiologic condition are known in the art. A number of IMDs of various types are known in the art for delivering electrical stimulating pulses to selected body tissue and typically comprise an implantable pulse generator (IPG) for generating the stimulating pulses under prescribed conditions and at least one lead bearing a stimulation electrode for delivering the stimulating pulses to the selected tissue. For example, cardiac pacemakers and implantable cardioverter-defibrillators (ICDs) have been developed for maintaining a desired heart rate during episodes of bradycardia or for applying cardioversion or defibrillation therapies to the heart upon detection of serious arrhythmias. Other nerve, brain, muscle and organ tissue stimulating medical devices are also known for treating a variety of conditions.

There are at least four paramount considerations or goals that are taken into account in the design and fabrication of IMDs. First, the IMD operation must be safe, reliable and effective in delivering a therapy and/or monitoring a physiologic condition. Second, the IMD must be long lived and be cost-effective relative to alternative therapies. Third, the IMD must be reasonably miniaturized so that it can be implanted without being uncomfortable and cosmetically distressing to the patient. Finally, each new generation of IMD must satisfy the first three considerations while providing an ever increasing number of performance features and functions that are clinically beneficial to the patient and useful to the medical community.

For example, over the past 20 years, ICD IPGs have evolved, as described in some detail in commonly assigned U.S. Pat. No. 5,265,588, from relatively bulky, crude, and short-lived ICD IPGs simply providing high energy defibrillation shocks to complex, long-lived, and miniaturized ICD IPGs providing a wide variety of pacing, cardioversion and defibrillation therapies. Numerous improvements have been made in cardioversion/defibrillation leads and electrodes that have enabled the cardioversion/defibrillation energy to be precisely delivered about selected upper and lower heart chambers and thereby dramatically reducing the delivered shock energy required to cardiovert or defibrillate the heart chamber. Moreover, the high voltage output circuitry has been improved in many respects to provide monophasic, biphasic, or multiphase cardioversion/defibrillation shock or pulse waveforms that are efficacious, sometimes with particular combinations of cardioversion/defibrillation electrodes, in lowering the required shock energy to cardiovert or defibrillate the heart.

The first implanted automatic implantable defibrillator (AID) IPG housing disclosed in U.S. Pat. No. 4,254,775 was very large and had to be implanted in a patient's abdominal region. Since that time, the ICD IPGs have been reduced in size while their complexity has been vastly increased. Battery energy requirements for powering both the low voltage integrated circuits (ICs) and for providing the cardioversion/defibrillation shocks have been reduced while battery energy density has been increased and battery configuration made more conforming to the interior space of the ICD IPG housing. Miniaturized, flat high voltage output capacitors that can be shaped to fit the allocated housing space and miniaturized high voltage switching components have been developed and employed. All of these improvements, together with the above-mentioned cardioversion/defibrillation improvements have contributed to a significant reduction in the volume of the ICD IPG housing without sacrificing longevity and capabilities. Similar improvements in reducing housing volume have been made in other IMD IPGs, particularly implantable cardiac pacemakers, nerve stimulators and monitors, over the same time period.

Such ICDs as well as implantable cardiac pacemakers and implantable cardiac monitors have been clinically employed or proposed that include capabilities of sensing one or more physiologic parameter and triggering delivery of a therapy and/or storage of physiologic data. With the exception of certain subcutaneously implanted monitors, all such IMDs comprise a hermetically sealed IPG housing containing the battery and electronic circuitry that is coupled through an elongated lead to a remote sense/stimulation electrode or physiologic sensor located typically in a heart chamber, heart muscle or blood vessel. Such physiologic parameters include electrical heart signals and other physiologic parameters, e.g. blood pressure at various locations of the heart and vascular system, respiration, blood temperature, blood pH, and blood gas concentrations.

The sensing of these physiologic parameters involves the detection of minute electrical signals in an inherently electrically noisy environment including both ambient EMI in the patient's environment as well as electrical signals either generated in the body or in the sensor due to patient motion or respiration or the like. Sources of EMI include metal detectors such as are used in airports, welders, radio transmitters (broadcast and two-way), cellular phones, microwave ovens, electronic article surveillance (EAS) systems, etc. The electrical signals conducted to the implanted device from the electrodes implanted in the heart may thus include EMI superimposed on the heart's natural cardiac signal. In dual chamber cardiac pacing and ICDs, it is necessary to sense and discriminate between P-waves and R-waves despite the presence of EMI and various pathologic cardiac conditions that can cause the sense amplifier to oversense or undersense these particular signals. It is currently the practice to start blanking periods upon delivery of a pacing pulse in one heart chamber to avoid saturating the sense amplifier circuitry and refractory periods that are used to disregard sense events representing artifacts of the induced depolarization or a closely timed depolarization in another heart chamber. To avoid sensing EMI, it has been the practice to low pass filter the sense amplifier input and to programmably adjust the sensitivity of the sense amplifier to a level that renders it insensitive to low level EMI but capable of sensing the peak voltages of the signal of interest. Descriptions of various sensing windows and noise rejection techniques for implantable and external pacemakers that have been employed or proposed are set forth in U.S. Pat. Nos. 4,357,943, 4,390,020, 4,401,119, 4,436,093, 4,596,292, and 5,188,117.

Although the IMD sense amplifiers are filtered to attenuate noise superimposed on a cardiac signal, in some situations the noise component may be such that the filters cannot adequately eliminate the noise. If a patient with an IMD walks through a metal detector, for example, the resulting EMI signal may overwhelm the cardiac signal picked up by the electrodes. Although the IMD may be able to determine that it is receiving an excessive amount of noise, the IMD may be unable to extract the true cardiac signal from the noise. Because the true cardiac electrical signal cannot be accurately ascertained, the IMD's operating system cannot determine when the vulnerable period of each cardiac cycle is occurring. Such implantable cardiac pacemakers and ICDs having a pacing capability are therefore often supplied with a "reversion mode" of operation that will cause no harm to the patient. However, the reversion mode also cannot provide the optimum pacing therapy that the patient may require at that very same time, and patient safety or comfort may be compromised. In the context of an ICD, the inability to distinguish high level EMI from a malignant tachyarrhythmia could either cause a mistaken delivery of a cardioversion/defibrillation shock or inhibit delivery of a warranted cardioversion/defibrillation shock.

The expansion of wireless communication modes occupying more and more frequency bands will continue to cause new EMI caused oversensing, undersensing, and inhibition problems to develop. It is expected that potential EMI frequencies will include those used by cellular phones, wireless phones, mobile radio, amateur (ham) radio, radar, ISM, wireless LAN, Bluetooth, HomeRF, broadcast AM, FM, UHF, and VHF signals, and MRI scans, etc. Interference sources and frequency bands employed will vary from country to country. See for example, "Influence of D-Net (European GSM-Standard) Cellular Phones on Pacemaker Function in 50 Patients with Permanent Pacemakers", by Wilke et al. (PACE, vol. 19, pp. 1456–8, October 1996) and "Pacemaker Inhibition and Asystole in a Pacemaker Dependent Patient", by Yesil et al. (PACE, vol. 18, p. 1963, October 1995). Potential EMI sources transmit in the 820–896 MHz, 1.93–1.99 GHz, and 2.402–2.48 GHz bands.

Therefore, there remains a need to improve the ability to sense low level cardiac signals in the presence of high level EMI in order to optimize IMD operation during EMI.

Similar problems can be caused by high level EMI that is superimposed onto lead conductors extending between remote physiologic sensors and the signal processing circuitry within the IMD housing. The lead conductors are used to conduct power to remote sensors or transducers and to conduct physiologic signals developed by the powered sensors or transducers back to the signal processing circuitry. Commonly assigned U.S. Pat. No. 5,535,752 describes such a combination of a pressure and temperature sensing lead and circuitry for powering the remote sensors or transducers and processing their signals. High level EMI signals superimposed on the physiologic signals can introduce errors into the signal processing, resulting in erroneous stored physiologic data or an inappropriate therapy delivery.

Therefore, there remains a need to improve the ability to sense low level physiologic sensor signals in the presence of high level EMI in order to optimize IMD operation during EMI.

In addition, such EMI can disrupt the programming or interrogation of an IMD. An ever increasing variety of programmable operating modes and monitoring and physiologic data collection capabilities have been incorporated into IMDs. Remote programming and interrogation of IMD operating modes and parameters have been implemented in the above-described IMDs employing uplink (from the IMD) and downlink (to the IMD) telemetry transmissions between an RF transceiver within the IMD and an external transceiver of an external "programmer". Such programmers are used to program the IMD by downlink telemetry transmission of commands that are received and stored in memory incorporated within the IMD that change an operating mode or parameter value governing a function performed by the IMD.

Both non-physiologic and physiologic data (collectively referred to herein as "patient data") can be transmitted by uplink RF telemetry from the IMD to the external programmer or through the patient's body to another IMD. The physiologic data typically includes stored and real time sampled physiologic signals, e.g., intracardiac electrocardiogram amplitude values, and sensor output signals. The non-physiologic patient data includes currently programmed device operating modes and parameter values, battery condition, device ID, patient ID, implantation dates, device programming history, real time event markers, and the like. In the context of implantable pacemakers and ICDs, such patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies.

The RF telemetry transmission system that evolved into current common usage relies upon magnetic field coupling through the patient's skin of an IMD IPG antenna with a closely spaced programmer antenna. Low amplitude magnetic fields are generated by current oscillating in an LC circuit of an RF telemetry antenna of the IMD or programmer in a transmitting mode. The currents induced in the closely spaced RF telemetry antenna of the programmer or IMD are detected and decoded in a receiving mode. Short duration bursts of the carrier frequency are transmitted in a variety of telemetry transmission formats. In the MEDTRONIC® product line, the RF carrier frequency is set at 175 kHz, and the IMD RF telemetry antenna located within the IMD housing is typically formed of coiled wire wound about a bulky ferrite core.

There are a number of limitations in the current MEDTRONIC® telemetry system employing the 175 kHz carrier frequency. First, using a ferrite core, wire coil, RF telemetry antenna results in a very low radiation efficiency because of feed impedance mismatch and ohmic losses and a magnetic field strength attenuated proportional to distance. These characteristics require that the implantable medical device be implanted just under the patient's skin and preferably oriented with the RF telemetry antenna closest to the patient's skin so that magnetic field coupling is provided. To ensure that the data transfer is reliable, it is necessary for the patient to remain still and for the medical professional to steadily hold the RF programmer head against the patient's skin over the IMD for the duration of the transmission. The time delays between downlink telemetry transmissions depend upon the user of the programmer, and there is a chance that the programmer head will not be held steady. If the uplink telemetry transmission link is interrupted by a gross movement, it is necessary to restart and repeat the uplink telemetry transmission.

In addition, it is necessary to insure that the IMD is not inadvertently mis-programmed by EMI that the patient is exposed to that could mimic the modulated 175 kHz carrier frequency. The classic manner of preventing the reception of such signals has been to disable the telemetry transceiver unless a magnetically sensitive reed switch within the IMD housing is switched open or closed by an externally applied permanent magnet field held over the IMD. Moreover, the application of the magnet traditionally only takes place during programming and interrogation telemetry sessions initiated in the presence of a medical professional. In certain IMDs, the patient is provided with a magnet that he or she can apply when experiencing symptoms to trigger delivery of a therapy and/or storage of physiologic data.

The RF telemetry data transmission rate is limited employing a 175 kHz carrier frequency. As device operating and monitoring capabilities multiply, it is desirable to be able to transmit out ever increasing volumes of data in real time or in as short a transmission time as possible with high reliability and immunity to spurious noise. Also, in an uplink telemetry transmission from an IMD, it is desirable to limit the current drain from the implanted battery as much as possible, simply to prolong IMD longevity.

As a result of these considerations, IMD-programmer RF telemetry schemes have been proposed having the objectives of conserving space within the IMD housing, eliminating the need for the close, steady magnetic field coupling to enable uplink and downlink telemetry transmission at a greater distance, increasing the data transmission rate, and minimizing battery consumption. The uses of the 204–216 MHz band and the 902–908 MHz ISM band have been proposed in U.S. Pat. Nos. 5,944,659 and 5,767,791 for telemetry transmissions between externally worn patient monitors and fixed location networked transceivers for ambulatory patient monitoring in a hospital context. The frequency bands that will be available for high frequency telemetry transmissions with IMDs can vary from country to country, and the sources and bandwidths of EMI can also vary from country to country.

The majority of front end high Q band pass filters used in radio frequency (RF) and intermediate frequency (IF) stages of heterodyning transceivers use off-chip, mechanically resonant components such as crystal filters or surface acoustic wave (SAW) signal transmission systems. These greatly outperform comparable devices using transistor technologies in terms of insertion loss, percent bandwidth, and achievable rejection of noise signals. In SAW resonators, signal processing can be combined with spread spectrum filtering for low transmission power and high rejection against jamming and interference. Advantages are high sensitivity, high reliability, and a moderate size of 1 cm$^3$.

Off-chip components are required to interface with integrated components at the board level, which constitutes an important bottleneck to miniaturization and the performance of heterodyning transceivers. Recent attempts to achieve single chip transceivers have used direct conversion architectures, rather than heterodyning and have suffered in overall performance. The continued growth of micromachining technologies, which yield high—Q on-chip vibrating mechanical resonators now make miniaturized, single-chip heterodyning transceivers possible. Microelectromechanical systems (MEMS) resonators yield ultra high Qs of over 80,000 under vacuum and center frequency temperature coefficients less than 10 ppm/° C. and serve well as a substitute for crystal filters and SAW devices in a variety of high-Q oscillator and filtering applications. MEMS resonators are capable of frequency operation to GHz levels and filtering operation up to the 6$^{th}$ order.

There remains a need to block such sources of EMI from contaminating or jamming uplink and downlink telemetry transmissions employing such high frequency RF operating channels.

The use of low pass, band pass and high pass filters remains desirable to pass desirable signals and to block or attenuate EMI. Ideally, EMI blocking filters employed in IMDs would be passive, low power consuming, and small in size. One approach proposed more recently for low pass filters involves the incorporation of discrete chip or discoidal capacitors with feedthroughs extending through the hermetically sealed housing wall, as disclosed in commonly assigned U.S. Pat. No. 5,836,992. Such filter capacitors are electrically connected between the feedthrough pins that couple the circuitry of the IMD with the lead conductors and externally disposed telemetry antenna and the feedthrough ferrules attached to the housing. The capacitor values are chosen to block frequencies in excess of 1 MHz.

It would be more desirable to provide band pass filtering to reject or attenuate signal frequencies above and below the characteristic frequencies of a signal of interest. The use of narrow band pass notch filters formed of passive components in external or implantable pacemakers to block EMI but to pass low frequency heart P-waves and R-waves has been suggested but not employed in the above-referenced '093 and '117 patents. It is observed therein that notch filters formed of discrete inductors and capacitors into passive analog circuits are unsuitable for such uses due to circuit complexity, difficulty in controlling component tolerances, component drift with temperature and aging, and high current drain. In the context of an IMD, assembling complex notch filters from bulky discrete inductors also consumes valuable space within the limited confines of the IMD housing. Accordingly, the use of active notch filters tuned specifically to pass a narrow frequency bandwidth and to block higher and lower frequency signals is proposed in the above-referenced '093 patent for an external cardiac pacemaker, where space is readily available and current consumption is less critical, since the battery is readily replaceable when spent.

In the '117 patent, it is also suggested that the formation of a suitable notch filter from integrated circuit (IC) components is not feasible. Instead, use of a delta modulator and band pass filter to digitize the signal from the sense amplifier initial stage and then digitally notch filter the digitized samples to remove any EMI artifacts. This approach does not work well in an IMD because the high frequency clock rate that would be required to sample and digitize the signal to remove high frequency EMI would consume battery current at an unacceptable rate and shorten battery life.

In order to fit within a minimal space, all electronic circuits of the IMD circuitry are preferably formed as ICs, but implementation of RF telemetry circuitry has required use of discrete capacitors and inductors mounted along with the RF IC to a circuit board. The number of such discrete inductors and capacitors is not reduced, but is actually increased, in the above-described high frequency, high data transmission rate telemetry transceiver circuitry. The relocation of the bulky RF telemetry antenna to a less critical area outside the hermetically sealed IMD housing is necessary to operate in a high frequency RF telemetry bandwidth and reduces space requirements. However, the discrete inductor and capacitor components mounted with one or more IC chip to an RF IC module substrate render the RF module unduly large such that it occupies a substantial portion of the volume within the IMD housing.

SUMMARY OF THE INVENTION

The present invention is directed to an IMD having a hermetically sealed chamber defined by a hermetically sealed housing, wherein the housing has an inner and an outer wall surface of a predetermined contour and enclosing a housing cavity or chamber of a predetermined volume. In accordance with a basic aspect of the present invention, the circuitry of the IMD comprises at least one IC chip mounted on a substrate and a plurality of micro-machined IC fabricated inductors and capacitors combined to form a notch filter or IC fabricated MEMS notch filter structures that reduces the space occupied within the housing. They can be tuned to block passage of particular EMI frequencies, and a plurality of the notch filter circuits can be combined to block a plurality of such EMI frequencies.

The miniaturized notch filters make the IMD operation safer, more reliable and more effective in delivering a therapy and/or monitoring a physiologic condition by blocking the EMI frequencies. Secondly, the miniaturized, passive notch filters do not increase current consumption and can be fitted within the hermetically sealed housing, thereby enabling inclusion of additional device functions that are clinically beneficial to the patient and useful to the medical community. The space within the IMD housing can be occupied by other components or can result in making the housing itself smaller and possibly thinner in profile than it would otherwise be.

In a first aspect of the invention, IC fabricated inductors are integrated into one or more IC chips mounted to circuit module substrates. In a further aspect of the invention, discrete capacitors are surface mounted over IC chips to reduce space taken up on the module substrate and to shorten the conductive paths between the IC and the capacitor. In a still further aspect of the invention, each IC chip is mounted into a well of the module substrate and short conductors are employed to electrically connect bond pads of the module substrate and the IC chip.

The inductors are preferably fabricated as planar spiral wound conductive traces formed of high conductive metals to reduce trace height and width while maintaining low resistance, thereby reducing parasitic capacitances between adjacent trace side walls and with a ground plane of the IC chip. The spiral winding preferably is square or rectangular, but having truncated turns to eliminate 90° angles that cause point-to-point parasitic capacitances.

The planar spiral wound conductive traces are further preferably suspended over the ground plane of the RF module substrate by micromachining underlying substrate material away to thereby reduce parasitic capacitances.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other features and advantages of the invention will become apparent to those skilled in the art from the following detailed description of a preferred embodiment, especially when considered in conjunction with the accompanying drawings in which.

DETAILED DESCRIPTION OF THE PREFERRED EMBODIMENTS OF THE INVENTION

The present invention can be implemented in any IMD having at least one of high frequency RF telemetry capabilities, electrical signal sense capabilities or physiologic sensor signal processing capabilities. The present invention will be described in relation to a particular IMD operating system design incorporating all three capabilities, but it is not intended that the invention be limited to that particular combination when it can be advantageously implemented in various types of IMDs incorporating fewer than all of these capabilities. At present, a wide variety of IMDs are commercially released or proposed for clinical implantation. Such medical devices include implantable cardiac pacemakers as well as ICDs, pacemaker-cardioverter-defibrillators, drug delivery pumps, cardiomyostimulators, cardiac and other physiologic monitors, nerve and muscle stimulators, deep brain stimulators, cochlear implants, artificial hearts, etc. As the technology advances, IMDs become ever more complex in possible programmable operating modes, menus of available operating parameters, and capabilities of monitoring increasing varieties of physiologic conditions and electrical signals. It is also contemplated that the present invention may be implemented in more than one IMD implanted within the same patient to enable communication between them.

Figure 1:
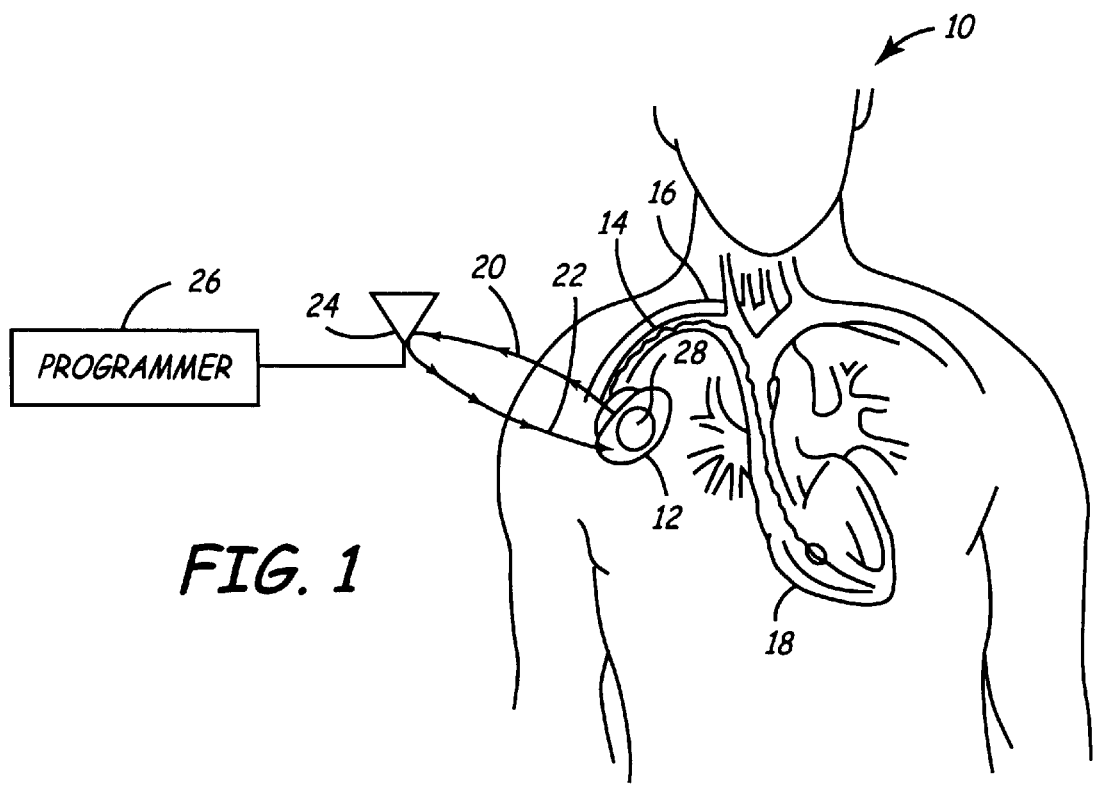
FIG. 1 is a simplified schematic view of an IMD constituting a cardiac pacemaker or ICD and an external programmer employing the improved RF telemetry antenna of the present invention.

FIG. 1 illustrates bi-directional telemetry communication between an external programmer 26 and an IMD 100, e.g., an ICD, hemodynamic monitor or cardiac pacemaker IPG 12 and an endocardial lead 14, in accordance with one embodiment of the present invention. The IPG 12 is implanted in the patient 10 beneath the patient's skin or muscle and is typically oriented to the skin surface. The IPG 12 is electrically coupled to the heart 18 of the patient 10 through pace/sense or cardioversion/defibrillation electrodes and lead conductor(s) of at least one endocardial lead 14 coupled to the IPG connector in a manner known in the art. The IPG 12 contains a battery and an operating system powered by the battery that may employ a microcomputer or a digital state machine for timing and controlling device functions in accordance with a programmed operating mode. The operating system includes memory registers in RAM for storing a variety of programmed-in operating mode and parameter values that are used by the operating system. The memory registers may also be used for storing data compiled from sensed cardiac activity and/or relating to device operating history or sensed physiologic parameters for telemetry out on receipt of a retrieval or interrogation instruction.

When the IPG 12 is provides cardiac pacing functions, its operating system also includes sense amplifiers for detecting cardiac signals, pulse generating output circuits for delivering pacing pulses to at least one heart chamber of the heart 18, and optionally includes patient activity sensors or other physiologic sensors for sensing the need for cardiac output and modulating pacing parameters accordingly through many alternative approaches set forth in the prior art. When the IPG 12 is an ICD, it includes one or more high power cardioversion/defibrillation output capacitor, electronic circuitry coupled to the sense amplifiers for detecting and discriminating pathologic and/or nonpathologic arrhythmias from one another and providing other functions, high voltage electronic charging circuitry for charging the output capacitor(s) from a battery voltage to a higher voltage, and electronic switching circuitry for dumping the charge built up on the output capacitor(s) through the cardioversion/defibrillation electrodes. Such a pacing or ICD IPG 12 is described in detail in commonly assigned U.S. Pat. No. 5,626,620 or 5,931,857, respectively.

The IPG operating system also includes telemetry circuitry and a telemetry antenna 28, which typically include relatively bulky discrete components described further below. The IPG telemetry antenna 28 can take the form of a surface mounted antenna described in the above-referenced '019 patent or an antenna enclosed within or mounted to the IPG connector. It is desirable to reduce the size of the IPG while increasing its functional capabilities and prolonging battery life to increase longevity. In accordance with the present invention, the current consumption of certain transceiver circuits is decreased to accomplish that goal. By way of background to place this in context, the IPG telemetry system and functions are first described as follows. For convenience of description, the preferred embodiment is described as follows using short range RF downlink telemetry (DT) transmissions 22 and uplink telemetry (UT) transmissions 20, but the invention and following claims are not be interpreted as so limited. Similarly, the terms "telemeter", "telemetry transmission" and the like are intended to embrace any such action and manner of communicating and conveying data and commands between the IPG and any external monitoring device or programmer 26 in the UT direction and the DT direction.

Programming commands or data are transmitted between the IPG RF telemetry antenna 28 within or on a surface of the IPG 12 and an external RF telemetry antenna 24 associated with the external programmer 26. Preferably, a high frequency carrier signal in the range of 402 to 405 MHz is employed and it is not necessary that the external RF telemetry antenna 24 be contained in a programmer RF head so that it can be located close to the patient's skin overlying the IPG 12. Instead, the external RF telemetry antenna 24 can be located on the case of the external programmer some distance, e.g., about two to five meters, from the patient 10. For example, the external programmer 26 and external RF telemetry antenna 24 may be on a stand a few meters or so away from the patient 10 as described, for example, in the above-referenced '019 patent and in commonly assigned U.S. Pat. Nos. 5,683,432 and 5,843,139. Moreover, the patient 10 may be active and could be exercising on a treadmill or the like during an uplink telemetry interrogation of real time ECG or physiologic parameters. The programmer 26 may also be designed to universally program existing IPGs that employ the conventional ferrite core, wire coil, RF telemetry antenna of the prior art and therefore also have a conventional programmer RF head and associated software for selective use with such IPGs.

In an uplink telemetry transmission 20, the external RF telemetry antenna 24 operates as a telemetry receiver antenna, and the IPG RF telemetry antenna 28 operates as a telemetry transmitter antenna. Conversely, in a downlink telemetry transmission 22, the external RF telemetry antenna 24 operates as a telemetry transmitter antenna, and the IPG RF telemetry antenna 28 operates as a telemetry receiver antenna.

Figure 2:
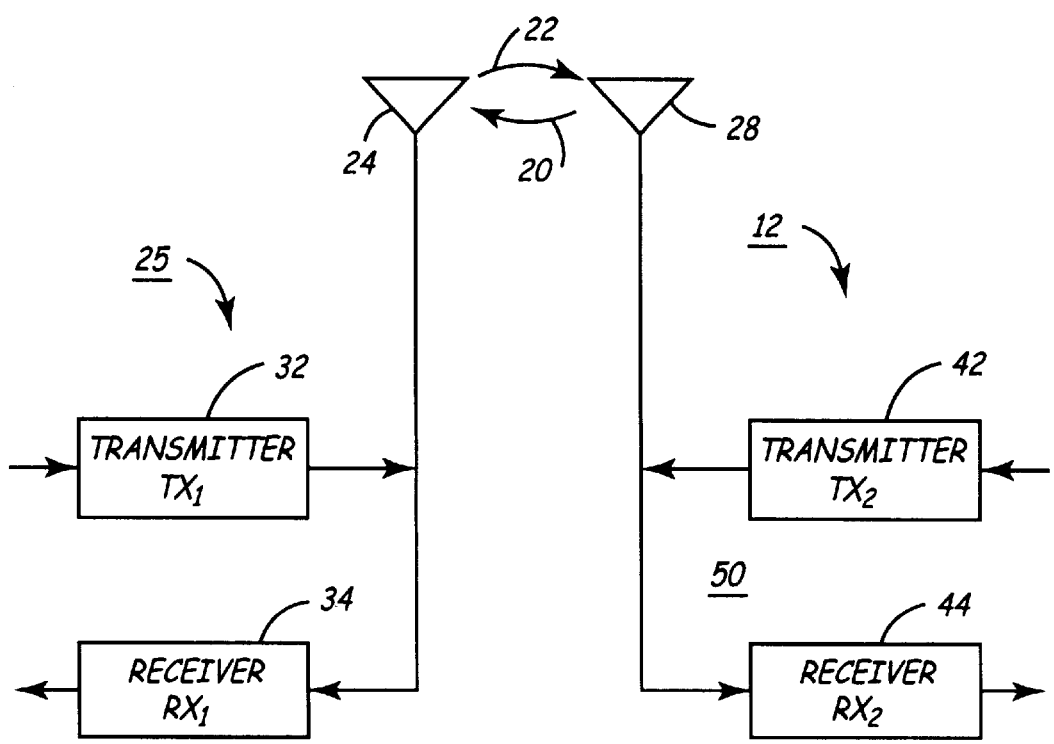
FIG. 2 is a simplified block diagram of major functional uplink and downlink telemetry transmission functions of the external programmer and IMD of FIG. 1.

FIG. 2 illustrates certain of the functional telemetry transmission blocks of the external programmer 26 and IPG 12 of FIG. 1. The external RF telemetry antenna 24 within the programmer 26 is coupled to a telemetry transceiver comprising a telemetry transmitter 32 and telemetry receiver 34. The programmer telemetry transmitter 32 and telemetry receiver 34 are coupled to control circuitry and registers operated under the control of a microcomputer and software as described in commonly assigned U.S. Pat. No. 5,843,139, for example. Similarly, within the IPG 12, the IPG RF telemetry antenna 28 is coupled to a telemetry transceiver comprising a telemetry transmitter 42 and telemetry receiver 44 incorporated into an IMD 100 described below with reference to FIGS. 3–6.

In an uplink telemetry transmission 20, the telemetered data may be encoded in any of the telemetry formats. In a particular example described below, the data encoding or modulation is in the form of frequency shift key (FSK) modulation of the carrier frequency, for example. To initiate an uplink telemetry transmission 20, the telemetry transmitter 32 in external programmer 26 is enabled in response to a user initiated INTERROGATE command to generate an INTERROGATE command in a downlink telemetry transmission 22. The INTERROGATE command is received and demodulated in receiver 44 and applied to an input of the IMD central processing unit (CPU), e.g. a microcomputer (not shown). The IMD microcomputer responds by generating an appropriate uplink data signal that is applied to the transmitter 42 to generate the encoded uplink telemetry signal 20.

The uplink and downlink telemetry transmissions follow a telemetry protocol that formulates, transmits and demodulates data packets each comprising a bit stream of frequency shift key (FSK) modulated data bits. A carrier frequency centered in a 300 kHz band between 402 MHz and 405 MHz is modulated in frequency or frequency shifted up representing a data bit "1" or shifted down to represent the data bit "0". The data packets are formulated of an FSK data bit stream with a preamble, data and error checking data bits.

Figure 3:
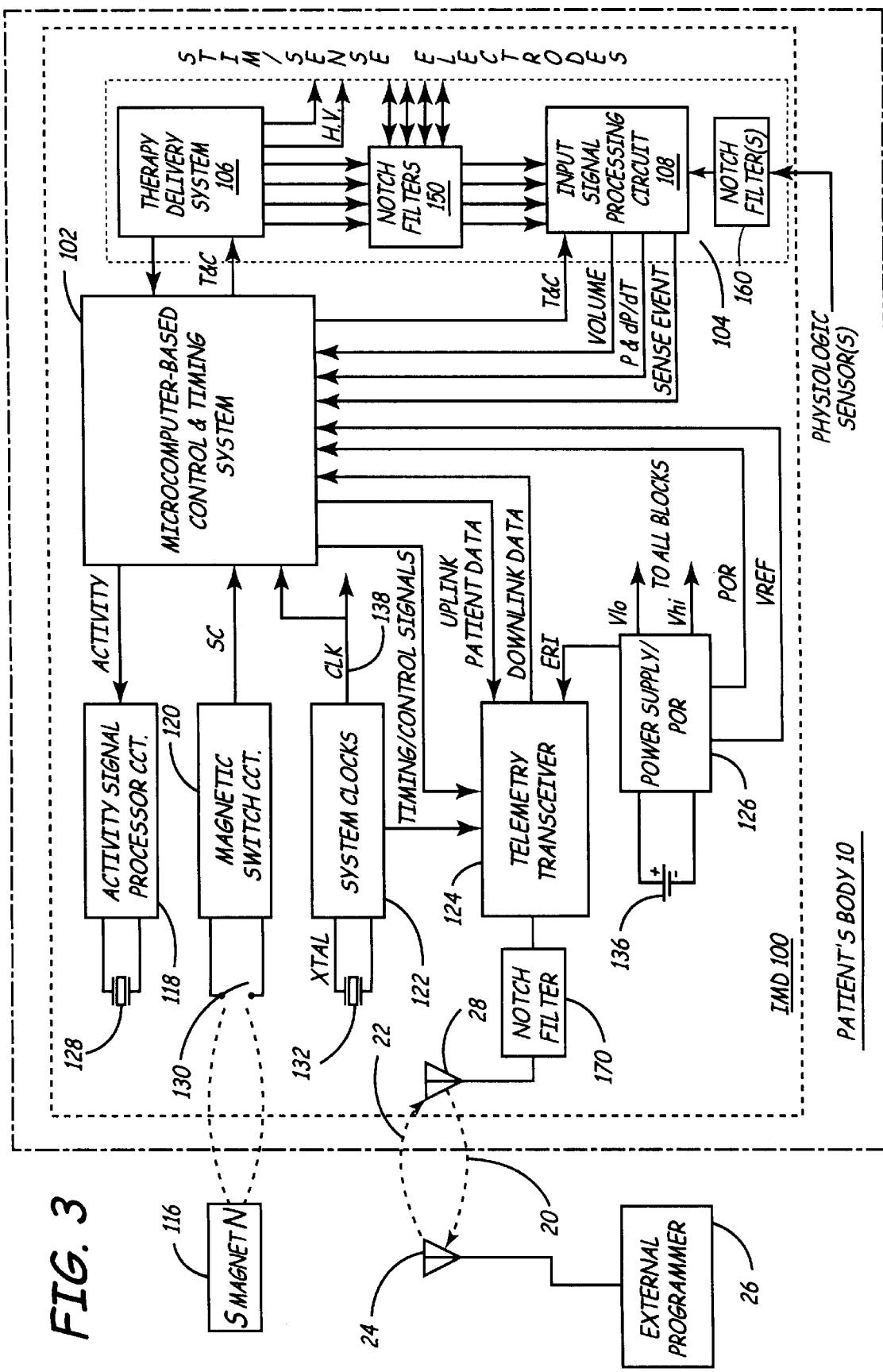
FIG. 3 is a block diagram of a system architecture of an exemplary IMD that incorporates delivery of a therapy and/or physiologic input signal processing in which notch filters of the present invention are incorporated.

FIG. 3 depicts a system architecture of an exemplary IMD 100 implanted into a patient's body 10 that provides delivery of a therapy and/or physiologic input signal processing. The typical IMD 100 has a system architecture that is constructed about a microcomputer-based control and timing system 102 which varies in sophistication and complexity depending upon the type and functional features incorporated therein. The functions of microcomputer-based IMD control and timing system 102 are controlled by firmware and programmed software algorithms stored in RAM and ROM including PROM and EEPROM and are carried out using a CPU, ALU, etc., of a typical microprocessor core architecture. The microcomputer-based IMD control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of IMD 100 can be accomplished with dedicated circuit hardware or state machine logic rather than a programmed microcomputer.

The IMD 100 also typically includes patient interface circuitry 104 for receiving signals from sensors or electrodes located at specific sites of a patient's body 10 and/or delivering a therapy to a site of the patient's body 10. The typical patient interface circuitry 104 therefore comprises a therapy delivery system 106 and a physiologic input signal processing circuit 108 or simply one or the other.

The therapy delivery system 106 can be configured to deliver electrical stimulation to the body, e.g., cardioversion/defibrillation shocks and/or cardiac pacing pulses delivered to the heart, or other electrical stimulation delivered to the brain, other organs, selected nerves, the spinal column, the cochlea, or muscle groups, including skeletal muscle wrapped about the heart. Or the therapy delivery system 106 can be configured as a drug pump delivering drugs into organs for therapeutic treatment or into the spinal column for pain relief. Or therapy delivery system 106 can be configured to operate an implantable heart assist device or pump implanted in patients awaiting a heart transplant operation.

It will be understood that most of these therapy delivery IMDs also have a physiologic input signal processing circuit 108 that processes physiologic signals that are used to trigger or modulate therapy delivery and are stored as physiologic signal data for later retrieval as described above. The physiologic input signal processing circuit 108 is coupled to electrical signal sense electrodes and/or physiologic sensors on or in the housing of the IMD 100 or situated at sites distanced from the IMD housing, typically in distal portions of elongated leads. The sensors or electrodes located outside the housing are coupled by conductors to feedthrough pins of feedthroughs extending through the housing wall. Certain physiologic sensors or sense electrodes can be mounted to a connector assembly so that the conductors are quite short. Typically, however, the conductors include the elongated conductors of leads extending to the remotely situated physiologic sensors and sense electrodes.

The IMD 100 can comprise an implantable cardiac monitor without a therapy delivery system 106, e.g., an implantable EGM monitor for recording the cardiac electrogram from electrodes remote from the heart as disclosed in commonly assigned U.S. Pat. No. 5,331,966 and PCT publication WO 98/02209. Or the IMD 100 can comprise an implantable hemodynamic monitor (IHM) for recording cardiac electrogram and other physiologic sensor derived signals, e.g., one or more of blood pressure, blood gases, temperature, electrical impedance of the heart and/or chest, and patient activity. The Medtronic® REVEAL® Insertable Loop Recorder having spaced housing EGM electrodes is an example of the former, and the Medtronic® CHRONICLE® IHM coupled with a capacitive pressure and temperature sensing lead and EGM sense electrodes of the type described in commonly assigned U.S. Pat. No. 5,564,434 is an example of the latter.

These are merely exemplary configurations of an IMD 100, a therapy delivery system 106, and a physiologic input signal processing circuit 108 for therapy delivery and/or monitoring. In all cases, the micro-computer-based control and timing system 102 governs all operating functions employing an appropriate, programmable operating algorithm. FIG. 3 also depicts other typical components common to an IMD 100 in any of these therapy delivery and/or monitoring configurations.

All current IMDs rely upon a source of electrical energy to power the IMD operating system including the circuitry of IMD 100 and to power any electromechanical devices, e.g., valves, pumps, etc. of a substance delivery IMD, or to provide electrical stimulation energy of an ICD shock generator, cardiac pacing pulse generator, or other electrical stimulation generator. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF sources, current sources, an elective replacement indicator (ERI) signal, and, in the case of an ICD, high voltage power Vhi to the therapy delivery system 106. Not all of the conventional interconnections of these voltages and signals are shown in FIG. 1.

In addition, in certain IMDs, an audible patient alert warning or message is generated by a transducer 128 when driven by a patient alert driver 118 to advise of device operations, battery power level or a monitored patient condition. In ICDs, the patient may be warned of the detection of a malignant tachyarrhythmia and the imminent delivery of a cardioversion/defibrillation shock to enable the patient to assume a resting position prior to delivery.

Virtually all current electronic IMD circuitry employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 3, each CLK signal generated by system clock 122 is routed to all applicable clocked logic via a clock tree 138. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers may be used for storing data compiled from sensed cardiac activity and/or relating to device operating history or sensed physiologic parameters for uplink telemetry transmission on receipt of a retrieval or interrogation instruction via a downlink telemetry transmission. The criteria for triggering data storage can also be programmed in via downlink telemetry transmitted instructions and parameter values The data storage is either triggered on a periodic basis or by detection logic within the physiologic input signal processing circuit 108 upon satisfaction of certain programmed-in event detection criteria. In some cases, the IMD 100 includes a magnetic field sensitive switch 130 that closes in response to a magnetic field, and the closure causes a magnetic switch circuit to issue a switch closed (SC) signal to control and timing system 102 which responds in a "magnet mode". For example, the patient may be provided with a magnet 116 that can be applied over the subcutaneously implanted IMD 100 to close switch 130 and prompt the control and timing system to deliver a therapy and/or store physiologic episode data when the patient experiences certain symptoms. In either case, event related data, e.g., the date and time, may be stored along with the stored periodically collected or patient initiated physiologic data for uplink telemetry in a later interrogation session.

In the IMD 100, uplink and downlink telemetry capabilities are provided to enable communication with either a remotely located external medical device or a more proximal medical device on the patient's body or another IMD in the patient's body as described above with respect to FIGS. 1 and 2. The stored physiologic data of the types described above as well as real-time generated physiologic data and non-physiologic data (collectively referred to herein as "patient data") can be transmitted by uplink RF telemetry from the IMD 100 to the external programmer or other remote medical device 26 in response to a downlink telemetered interrogation command. The real-time physiologic data typically includes real time sampled signal levels, e.g., intracardiac electrocardiogram amplitude values, and sensor output signals. The non-physiologic patient data includes currently programmed device operating modes and parameter values, battery condition, device ID, patient ID, implantation dates, device programming history, real time event markers, and the like. In the context of implantable pacemakers and ICDs, such patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies.

Figure 4:
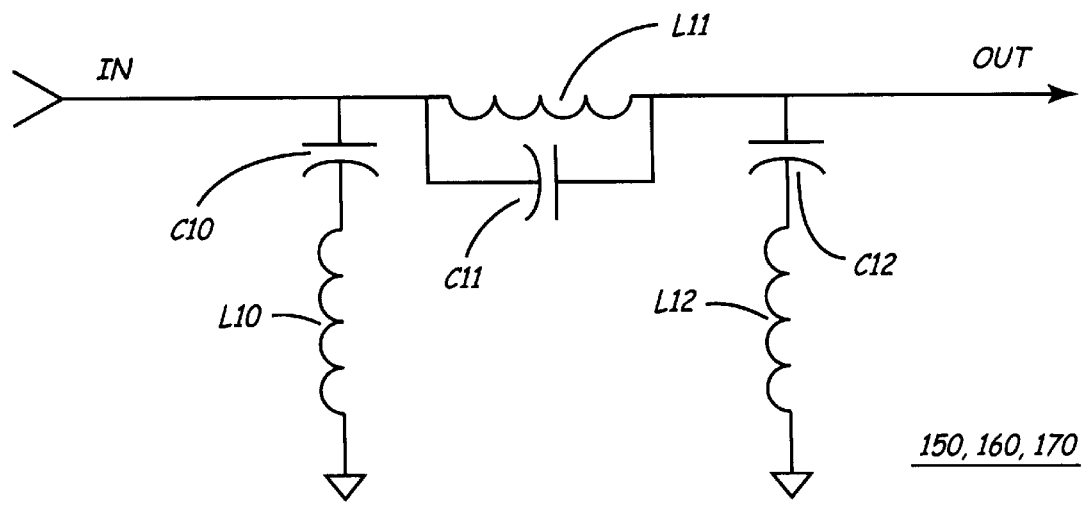
FIG. 4 is a circuit representation of a notch filter that is realized using either a MEMS notch filter or a plurality of IC fabricated inductors and discrete capacitors in accordance with the alternative embodiments of the invention.

The present invention provides at least one miniaturized, low current drain, passive notch filter 150 and/or 160 and/or 170 at the inputs to the physiologic input signal circuit 108 and the telemetry transceiver 124 that receive and process each respective signal as shown in FIG. 3. Each notch filter 150, 160, 170 is composed of miniaturized filter components which are either assembled into the circuit depicted in FIG. 4 or have an equivalent circuit to that depicted in FIG. 4 and specifically tuned to block a particular EMI source, such as a cell phone. The miniaturized filter components are either IC fabricated inductors L10, L11 and L12 and discrete capacitors C10, C11 and C12 coupled together as depicted in FIG. 4 or an IC fabricated MEMS resonator that has the same equivalent circuit. Moreover, each notch filter 150, 160, 170 can include a plurality of these miniaturized filter components connected electrically in series that are each tuned to block particular frequencies of EMI that a patient may be exposed to. The notch filter 150, 160 and 170 may also be combined with a band pass filter that is tuned to pass signal frequencies within a predetermined bandwidth of interest. The particular uses and characteristics of the notch filters 150, 160 and 170 illustrated in FIG. 3 will now be described, and the alternative fabrication methods will then be described.

With respect to the physiologic input signal processing circuit 108, it typically includes a plurality of electrical signal amplifier circuits which each amplify, process, and in some cases detect "sense events" from characteristics of an electrical sense signal or a sensor output signal. As described above, EMI can be superimposed upon the cardiac or other electrical signals of interest and physiologic sensor output signals that are conducted through the conductors and feedthrough pins to a particular sense circuit in the physiologic input signal processing circuit 108.

For example, the physiologic input signal processing circuit 108 in IMDs providing dual chamber or multi-site or multi-chamber monitoring and/or pacing functions includes a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave or R-wave, respectively and providing an ASENSE or VSENSE event signal to the control and timing system 102. Timing and control system 102 responds in accordance with its particular operating system to deliver or modify a pacing therapy, if appropriate, or to accumulate data for uplink telemetry transmission or to provide a Marker Channel® signal in a variety of ways known in the art.

In accordance with one aspect of the present invention, at least one miniaturized, low current consuming, notch filter circuit within notch filter 150 is placed in the input circuitry stage of each sense amplifier that senses P-waves or R-waves or processes the EGM. Each notch filter circuit within notch filter 150 is specifically tuned to block one or more particular EMI source, such as a cell phone or MRI or the like that a patient may be exposed to. The notch filter 150 may also be combined with a band pass filter that is tuned to pass signal frequencies within a predetermined bandwidth characteristic of the P-wave or R-wave from its input to its output and to block or attenuate other frequencies imposed on the signal conducted through the feedthrough pin and to its input.

In addition, the input signal processing circuit 108 includes at least one physiologic sensor signal processing channel for sensing and processing a sensor derived signal from a physiologic sensor located in relation to a heart chamber or elsewhere in the body. In accordance with this aspect of the present invention, at least one miniaturized, low current consuming, notch filter 160 is included in each such sensor signal processing channel. The notch filter 160 is interposed between a feedthrough pin and the input to the sensor signal processing circuit within input signal processing circuit 108. The notch filter 150 is tuned to block passage of signal frequencies within a predetermined notch bandwidth characteristic of the particular EMI source from its input to its output.

Figure 6:
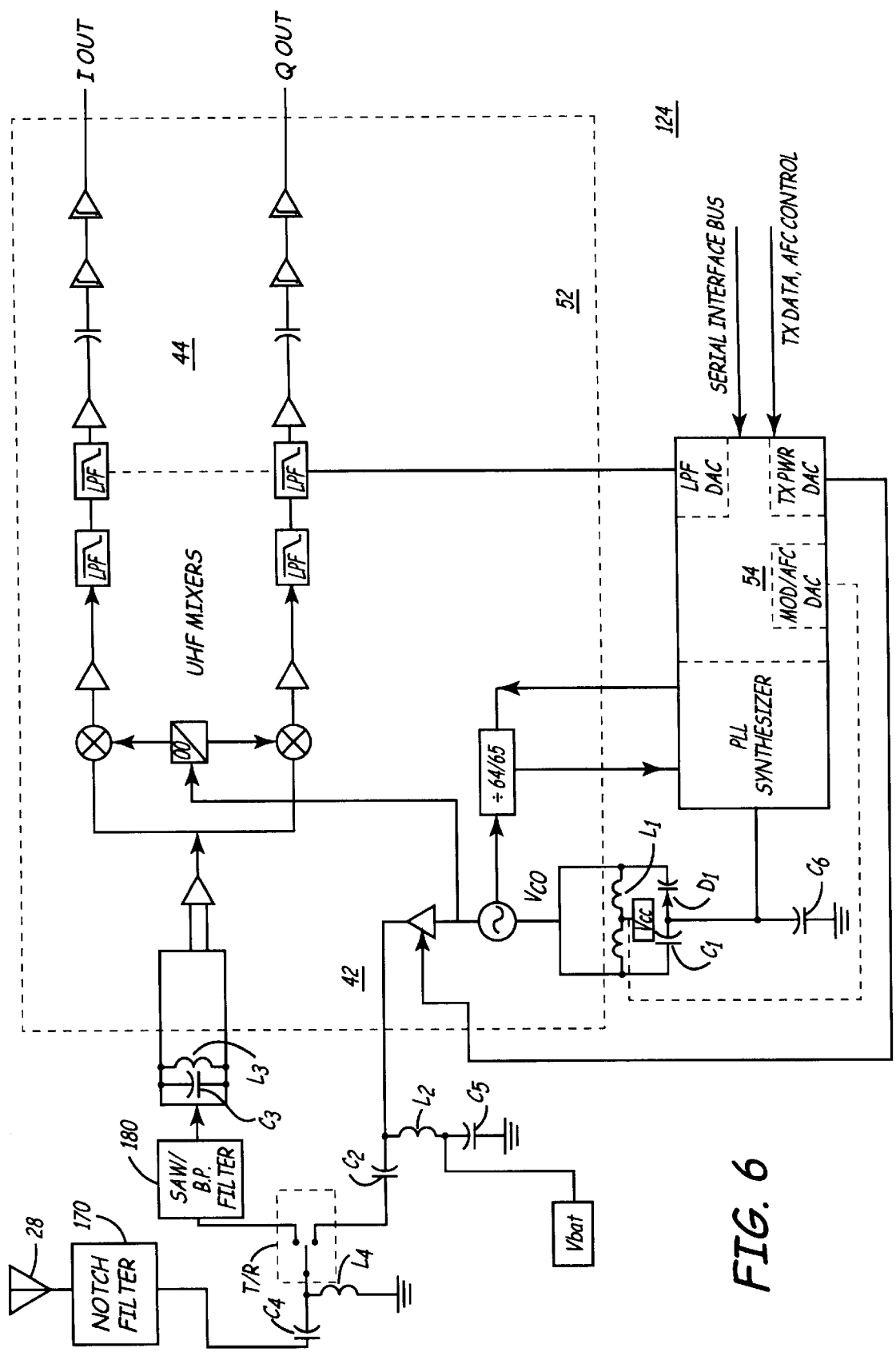
FIG. 6 is a simplified block diagram of a telemetry transceiver circuit of the IMD of FIG. 3.

Similarly, as described above, EMI can be superimposed upon the FSK modulated bit stream of a received downlink telemetry transmission, and so a further notch filter 170 is electrically connected between the telemetry antenna 28 and the telemetry transceiver 124. FIG. 6 further schematically depicts the IMD telemetry transceiver circuit 124 comprising an RF IC chip 52, an electronic control (ETC) chip 54, a number of discrete components identified and described further below that are, with the exception of antenna 28, assembled as an RF telemetry module. These components of the RF telemetry module are physically mounted to a miniaturized circuit board or substrate and electrically connected to bonding pads and conductor paths formed on the surface or extending through the circuit board. Electrical connections are made between certain of the substrate bonding pads and the control and timing system 102 or a feedthrough pin (not shown) extending through the IPG housing wall (not shown) and coupled to the IPG RF antenna 28. The printed circuit board or substrate is formed in the typical manners of epoxy-glass and polyamide flex printed wiring boards, ceramic substrates or silicon substrates that can be formed employing silicon wafer scale integration techniques.

The RF module is coupled with a hardware interface (not shown) comprises uplink and downlink RAM buffers, control and status registers, and interrupt lines as well as a synchronous serial bus, transmit and receive serial data lines, a frequency standard input to the phase detector and AFC control lines. The hardware interface includes a baseband receiver signal processor, a protocol physical layer controller, a CPU, and RAM and functions as the RF module controller and interface. In the receive mode, the baseband receiver signal processor implements an AFC frequency control of the VCO and provides bit synchronization and demodulation functions from the received data bit stream of each packet so that the received data is demodulated without errors. The protocol physical layer controller functions to detect the preamble of the packet and to perform CRC processing of the CRC data bits of the packet for both the transmit and receive operations.

FIG. 6 depicts the circuitry of the RF module within transceiver 124 of FIG. 3 including an RF IC chip 52, an electronic control (ETC) chip 54 and the discrete components that provide the functions of a "Zero IF" receiver 44, an FSK transmitter 42, a UHF Frequency Synthesizer providing both local oscillator injection to the UHF receiver's UHF Mixers, and a Frequency Shift Key (FSK) FM carrier for the FSK transmitter 42. In a" downlink telemetry receive mode, INPHASE (I) and QUADRATURE (Q) baseband IF signals are developed by the RF Mixers in the RF IC chip 52 that are forwarded for digital demodulation and bit sync and signal processing by the telemetry digital hardware 64. In an FSK uplink telemetry transmit mode, TX DATA is encoded in ETC chip 54 and uplink telemetered by FSK modulation of the carrier signal developed by a voltage controlled oscillator (VCO) resident in part on the RF IC chip 52 and in a tank circuit formed of discrete inductor L1, capacitor C1 and diode D1.

The ETC chip 54 is a mixed signal chip that provides a phase detector, charge pump, lock detector and programmable counters of the frequency synthesizer, an FSK modulator, an AFC control, current DACs for setup of the RF IC chip 52, and a controller interface. The discrete components of the RF module 50 include the phase lock loop (PLL) loop filter capacitor C1, inductor L1, tuning varactor diode D1, a surface acoustic wave (SAW) resonator or band pass filter 180, an antenna transmit/receive switch T/R and the notch filter 170. In addition, further discrete inductors L2, L3, L4 and capacitors C2, C3, C4, C5, C6 are required for proper circuit functions coupled to the antenna 28 directly or through the transmit/receive switch T/R or to the SAW or bandpass filter 180. Additionally, mutually coupled inductors, in the form of transformers, can be used as baluns to drive balanced circuits and also to provide direct and broadband impedance transformations. The transformer function could be used for driving diode bridges in balanced mixers and impedance matching from 50 ohm unbalanced impedances (i.e., antennas) to the higher, balanced, impedances present in low current RF ICs.

Figure 5:
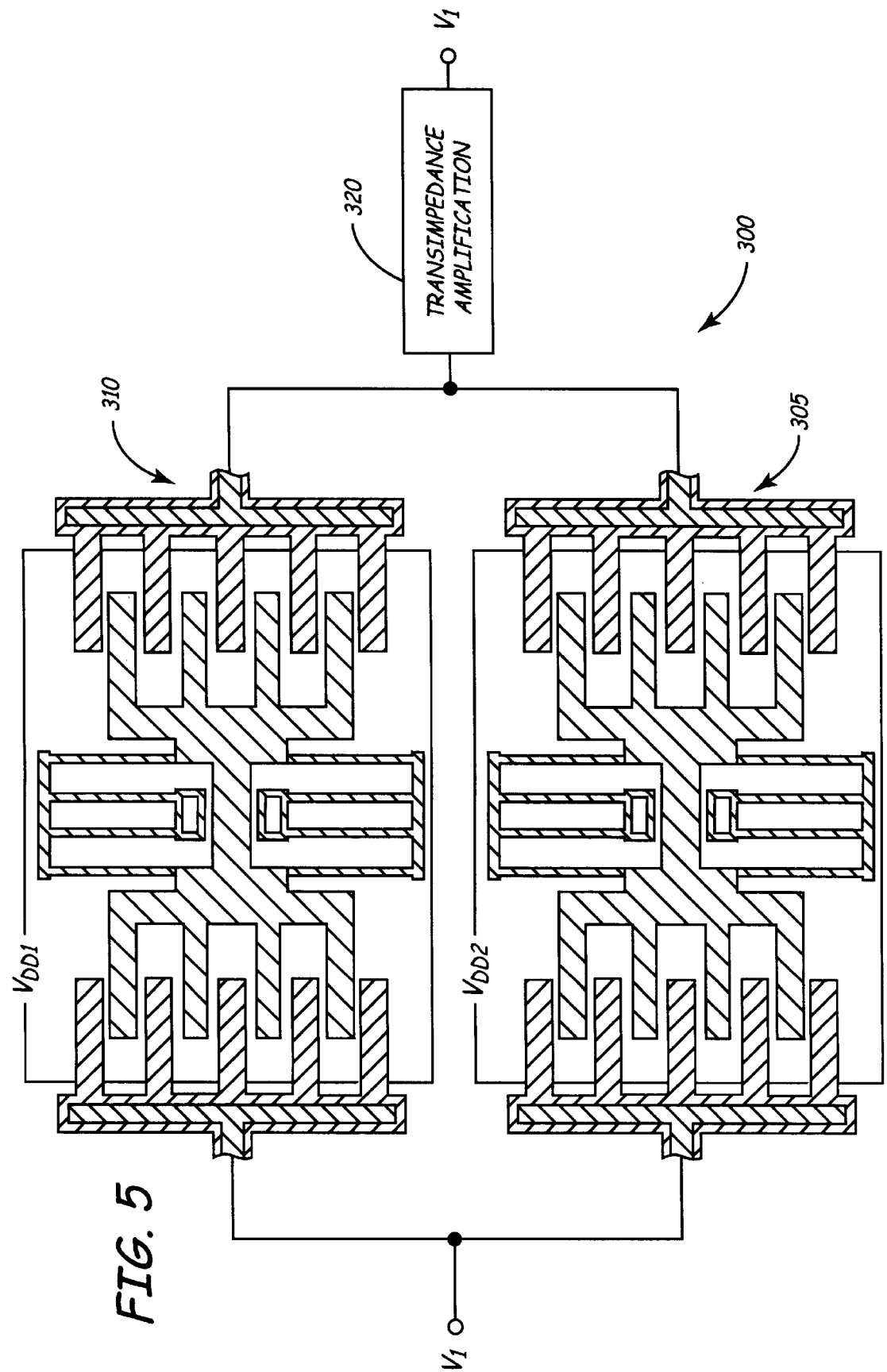
FIG. 5 is a depiction of one exemplary MEMS notch filter that is IC fabricated into an IC die.

As noted above, the miniaturized filter components of the notch filter 170 are either IC fabricated inductors L10, L11 and L12 and discrete capacitors C10, C11 and C12 coupled together as depicted in FIG. 4 or an IC fabricated MEMS resonator of FIG. 5 that has the same equivalent circuit.

In accordance with the present invention, at least the notch filters 150, 160 and 170 are formed of either IC fabricated inductors L10, L11 and L12 and discrete capacitors C10, C11 and C12 coupled together as depicted in FIG. 4 or an IC fabricated MEMS resonator of FIG. 5 that has the same equivalent circuit.

FIG. 5 provides a perspective view of an exemplary high-frequency MEMS notch filter 150,160,170 that is fabricated in a manner described in U.S. Pat. No. 5,537,083 and that can be IC fabricated within an IC chip to form the notch filter circuitry of notch filters 150, 160,170. The fabrication of various MEMS devices are also described in U.S. Pat. Nos. 5,455,547; 5,491,604; 5,589,082; and 5,839,062. The MEMS structure 300 depicted in FIG. 5 comprises a pair of resonators 305 and 310 electrically connected in parallel between a common input receiving signal $V_i$ and the input of a transimpedance amplification stage 320. Ground voltages $V_{DD1}$ and $V_{DD2}$ are applied to the ground planes beneath the two resonators 305 and 310, respectively. The current outputs of the two microresonators 305 and 310 are summed and directed to the transimpedance amplification unit 320 which produces an output signal $V_O$. If the resonant frequencies of the two microresonators 305 and 310 differ by a small amount, the output response is a notch filter since the signals are in-phase. The currents are out of phase by about 90° and cancel in the frequency interval between the resonances but combine outside this interval since the currents are in-phase.

Such an MEMS filter structure 300 can be IC fabricated to possess the desired notch filter characteristics for blocking a particular EMI frequency into a discrete IC chip for each such notch filter 150, 160, 170 or into one of the ICs also containing the input signal processing circuit 108 or an RF IC or other IC included within telemetry transceiver 124. As noted above, the MEMS filter structure 300 can be replicated with suitable tuning in such an IC to block a plurality of particular EMI frequencies.

A further aspect of the present invention involves IC fabrication of the inductors L10, L11 and L12 of each notch filter circuit included within notch filters 150, 160 and 170. A still further aspect of the present invention involves mounting the discrete capacitors over the exposed surface of an IC chip. Other inductors or capacitors employed in circuitry of the IMD 100 can be formed of IC fabricated inductors or can be mounted to an IC chip in the manner described below. In the illustrated example of FIG. 6, the inductors L1–L3 can also be incorporated into RF IC chip 52, and capacitors C1–C3 are mounted to RF IC chip 52. Capacitor C6 can be mounted to ETC chip 54, and a discrete IC can be provided for inductor L4 to provide for ready connection with the T/R switch. Alternatively, at least inductor L1 could be incorporated into and capacitor C1 could be mounted onto ETC chip 54.

According to conventional practice in IMD design and fabrication, inductors are not presently integratable into an IC due to a high value of parasitic capacitance to the substrate as $Q_p=Rp/(2*Pl*f*L)$ where Rp (parallel resistance) is due to intrinsic substrate conductivity. Another limiting factor in inductor Q is Rs or series resistance as $Q_s=(2*Pl*f*L)/Rs$. Series resistance, in this case, is primarily due to effective conductivity of the inductor's conductor (with skin effect and surface roughness effects included). Both effects must be included in determining the actual Q for the inductance $(Q_{actual}=1/((1/Q_s)+(1/Q_p))$.

Figure 7:
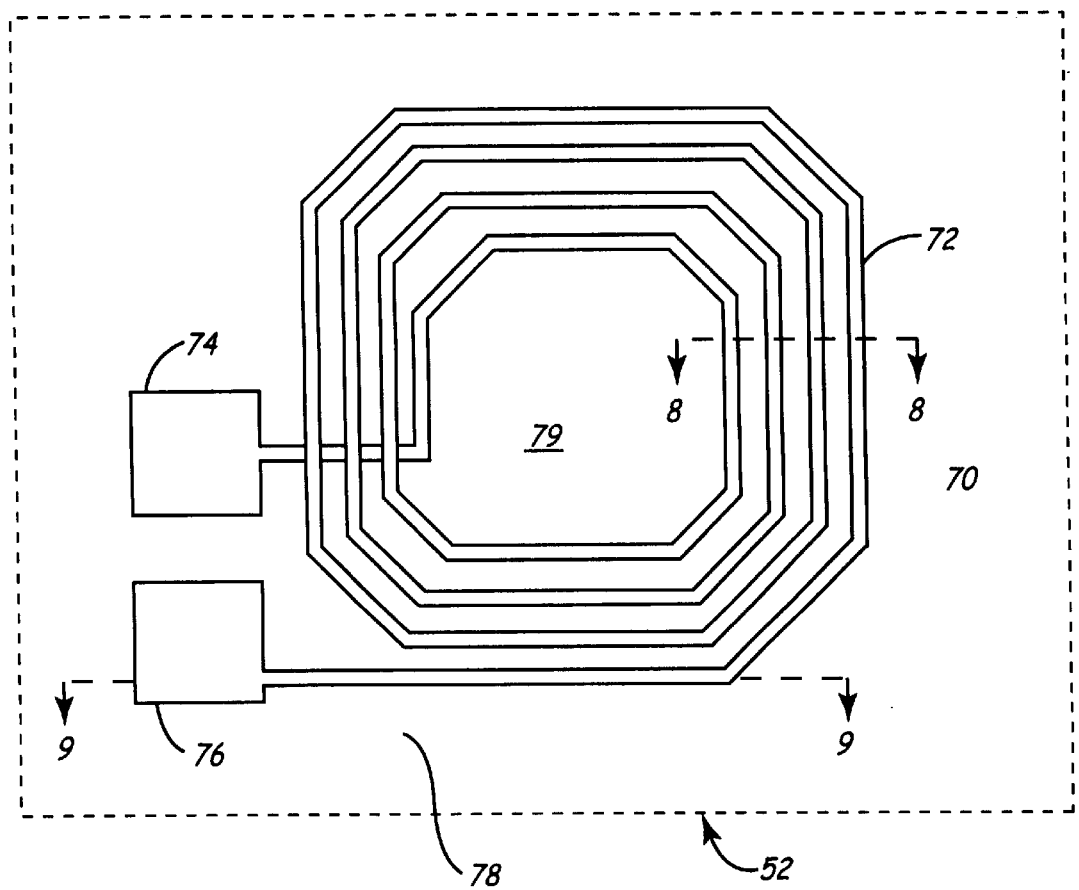
FIG. 7 is a schematic illustration of a spiral wound inductor formed by IC fabrication processes employed to form a notch filter.

However, it is feasible to fabricate certain of the high Q inductors by integration of inductors onto the surface of an ASIC IC, e.g., RF IC 52 and/or ETC IC 54, if certain design features and fabrication techniques are employed. Referring to FIG. 7, first, the design of the inductor 70 is in the shape of a planar spiral 72 formed on IC surface 78 extending between bonding pads 74 and 76 coupled to first and second ends of the planar spiral 72. The first end of the planar spiral 72 is coupled through a via to a conductive trace disposed below the IC surface 78 and extending laterally across the planar spiral 72 and is in turn coupled to the bonding pad 74 by way or a further via. These fabrication techniques are described, for example, in "RF Circuit design Aspects of Spiral Inductors on Silicon", Burghartz, et al., *IEEE Journal of Solid-State Circuits*, Vol 33, No. 12, December, 1998, pp. 2028–34 and in U.S. Pat. Nos. 5,793,272, 5,884,990, 6,054,329, 6,114,937, and 5,416,356.

The spiral turns of planar spiral 72 are arranged around an open central area 79 because tightly wound centrally disposed spirally wound central turns add significant resistance R without contributing any appreciable inductance L. Furthermore, the planar spiral 72 is implemented with diagonal corners to minimize impedance mismatch (and thus energy losses) of a right angle design.

Figure 8:
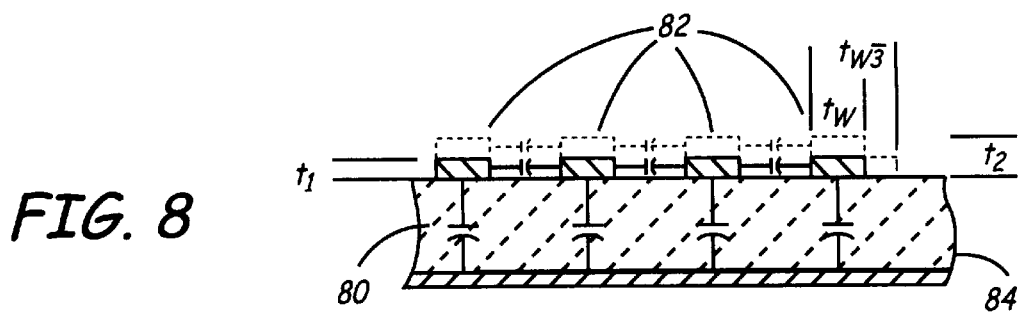
FIG. 8 is a partial cross-section view taken along lines 8—8 of FIG. 7 illustrating fabrication of the traces forming the spiral turns of the spiral inductor of FIG. 7.

The spiral turns are deposited as a continuous trace 82 on IC surface 78 or as a layer of IC substrate 80 preferably using a high conductivity conductor selected from the group consisting of gold, copper or aluminum-copper metallization instead of standard aluminum or aluminum silicide metallization. Copper has less than one-half the impedance of similar thickness aluminum. Therefore the thickness or wall height of the traces can be reduced as shown in FIG. 8 from the dotted line thickness $t_2$ to the solid line thickness $t_1$. The reduction in thickness or trace wall height using copper metallization also reduces wall-to-wall parasitic capacitance by one-half. Moreover, parasitic capacitance across IC substrate 80 to an underlying conductive ground plane 84 may be reduced 30% because the track width $t_w$ may be reduced to 70% of an equivalent aluminum track width $t_{wa}$ at the same impedance level.

Figure 9:
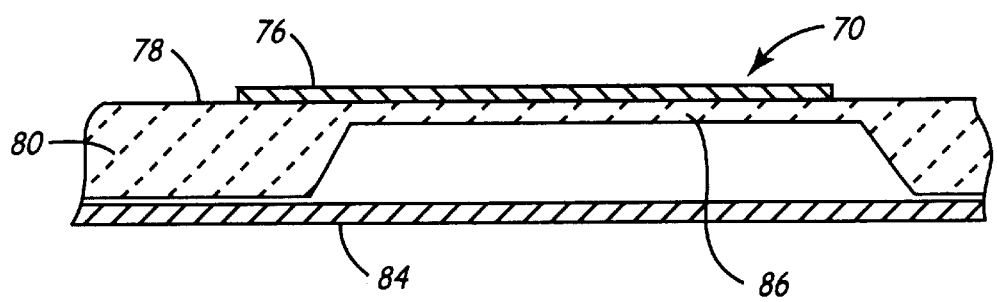
FIG. 9 is a partial cross-section view taken along lines 9—9 of FIG. 7 illustrating fabrication of the traces forming the spiral turns of the spiral inductor of FIG. 7 suspended on a platform.

Substrate capacitance of the inductor is additionally substantially reduced by the implementation of the spiral inductor 70 on a micromachined platform 86 as shown in FIG. 9. Additionally, a SOI substrate should optimally be used. A segmented ground plane 84 may optionally be added. The SOI substrate 80 is etched to a thin platform 86 by back etching as is known in the art and described, for example, in "Suspended SOI Structure for Advanced 0.1 $\mu$m CMOS RF Devices", Hisamoto, et al., *IEEE Transactions on Electron Devices*, Vol 45, No. 5, May 1998, pp. 1039–46. Leaving the thin platform 86 in place rather than fully etching the silicon substrate away makes the planar spiral 72 more readily producible and robust. However, it will be understood that the planar spiral 72 could be fully suspended without a planar support.

Figure 10:
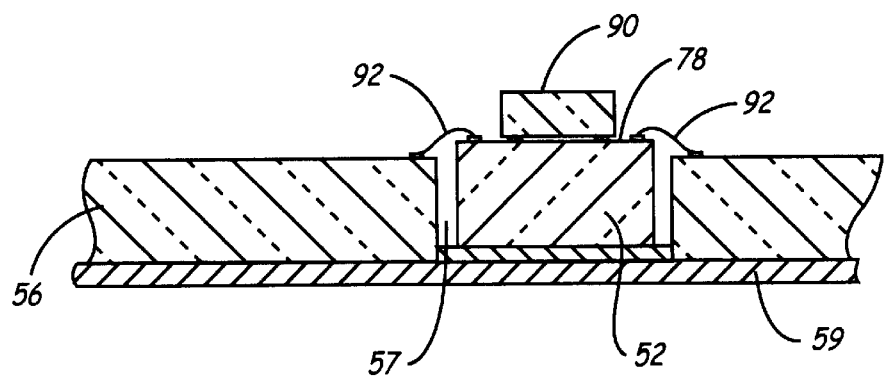
FIG. 10 is a side view in partial cross-section showing the mounting of the RF IC in a well of the RF module substrate and a discrete capacitor surface mounted to the RF IC surface, for example.

Additionally, chip inductor and capacitor integration may be accomplished by using "wafer scale integration" techniques whereby capacitor (or inductor) contact areas are integrated onto the surface of RF IC 52. FIG. 10 shows that the RF IC 52 is placed in a well 88 of the RF module substrate 56, and that a discrete capacitor 90 is fitted over it. The small chip capacitor 90 (such as 68 pF 0.01×0.01" Dielectric Labs, Inc., Part No. D10) can be soldered or epoxy attached directly to the surface 78 of the RF IC 52. This direct IC mounting eliminates substantial parasitic high frequency impedance, capacitance and/or inductance caused by IC routing to the edge of the die, wire bonds to the supporting substrate, substrate interconnect to substrate pads and substrate pads and allows the capacitors to be reduced in size. The capacitor body may be placed over active IC functional circuitry to further reduce die area. Additionally the RF IC 52 may be placed in a well 57 within RF module substrate 56 over substrate ground plane 59 to minimize the length of wire bond wires 92 and thereby reducing parasitic capacitance and inductance occasioned by longer wires required when the RF IC 52 is surface mounted to substrate 56.

Utilizing these fabrication techniques advantageously reduces the form factor (i.e., size, volume) of all the circuitry, minimizes substrate noise and/or coupling, improves performance, reduces fully allocated product costs (FAPC), and does not introduce any substantial packaging issues. Standard wafer fabrication processes can also be economically employed. Further articles relating to fabrication processes that can be employed include: "Micromachined Planar Spiral Inductor in Standard GaAs HEMT MMIC Technology", Ribas, et al., *IEEE Electron Device Letters*, Vol. 19, No. 8, August 1998, pp. 285–7; "Analysis, Design, and Optimization of Spiral Inductors and Transformers for Si RF IC's", Niknejad, et al., *IEEE Journal of Solid-State Circuits*, Vol 33, No. 10, October 1998, pp. 1470–81; "A Novel High-Q and Wide-Frequency-Range Inductor Using Si 3-D MMIC Technology", Kamogawa, et al., *IEEE Microwave and Guided Wave Letters*, Vol 9, No. 1, January 1999, pp. 16–18; "Integrated Circuit Technology Options for RFIC's—Present Status and Future Directions", Larson, *IEEE Journal of Solid-State Circuits*, Vol 33, No. 3, March 1998, pp. 387–99; and "Micromachined Electro-Mechanically Tunable Capacitors and Their Applications to RF IC's", Dec et al., *IEEE Transactions on Microwave Theory and Techniques*, Vol 46, No. 12, December 1998, pp. 2587–95.

These techniques can be employed to form IC fabricated inductors L10, L11 and L12 within an IC chip that is dedicated for use as a notch filter, and the capacitors C10, C11 and C12 mounted to the IC chip. In this manner, the notch filters 150, 160 and 170 can be separately fabricated and each may include a plurality of notch filter circuits each comprising IC fabricated inductors L10, L11 and L12 and discrete capacitors C10, C11 and C12 mounted to the IC chip. Alternatively, the discrete capacitors can be mounted to a circuit board and connected electrically with the IC fabricated inductors L10, L11 and L12.

All patents and other publications identified above are incorporated herein by reference.

While the present invention has been illustrated and described with particularity in terms of preferred embodiments, it should be understood that no limitation of the scope of the invention is intended thereby. The scope of the invention is defined only by the claims appended hereto. It should also be understood that variations of the particular embodiments described herein incorporating the principles of the present invention will occur to those of ordinary skill in the art and yet be within the scope of the appended claims.

What is claimed is:

1. An implantable medical device operable to perform a therapeutic and/or monitoring function in a living body while exposed to sources of electromagnetic interference (EMI) comprising:

a housing having a housing side wall and inner and outer wall surfaces of a predetermined contour enclosing a hermetically sealed chamber;

a battery enclosed within said hermetically sealed chamber; and electronic circuitry enclosed within said hermetically sealed chamber powered by the battery comprising a plurality of discrete components and at least one integrated circuit IC chip having an IC chip substrate and mounted to a circuit board dimensioned to fit within said hermetically sealed chamber along with said battery, said electronic circuitry comprising at least one notch filter having an input and output that blocks predetermined EMI signal frequencies while passing other signal frequencies from the input to the output, the notch filter formed of at least one IC fabricated inductor formed integrally with said IC chip.

2. The implantable medical device of claim 1, wherein the IC fabricated inductor comprises a planar spiral formed of a continuous, conductive, spiral trace extending between bonding pads that is deposited as a layer of the IC chip substrate, the spiral trace having turning points that are angled at less than 90° to reduce parasitic capacitance between adjacent turning points of the spiral trace.

3. The implantable medical device of claim 2, wherein the spiral trace and bonding pads consist of a high conductivity conductor selected from the group consisting of gold, copper and aluminum-copper metallization to reduce trace height and width to thereby reduce parasitic capacitances between adjacent turns of the trace and through the IC chip substrate.

4. The implantable medical device of claim 3, wherein the IC chip substrate further comprises a ground plane spaced from said planar spiral, and said continuous conductive trace extending between the bonding pads is deposited over an exposed surface of a suspended platform of the IC chip substrate formed by micromachining substrate material between the exposed surface of the suspended platform and the ground plane away, to thereby reduce parasitic capacitances between adjacent turns of the trace through the IC chip substrate to the ground plane.

5. The implantable medical device of claim 1, wherein the IC fabricated inductor comprises a planar spiral formed of a continuous, conductive, spiral trace extending between bonding pads that is deposited as a layer of the IC chip substrate, the spiral trace and bonding pads consist of a high conductivity conductor selected from the group consisting of gold, copper and aluminum-copper metallization to reduce trace height and width to thereby reduce parasitic capacitances between adjacent turns of the trace and through the IC chip substrate to the ground plane.

6. The implantable medical device of claim 5, wherein the spiral trace and bonding pads consist of a high conductivity conductor selected from the group consisting of gold, copper and aluminum-copper metallization to reduce trace height and width to thereby reduce parasitic capacitances between adjacent turns of the trace and through the IC chip substrate.

7. The implantable medical device of claim 1, wherein the IC fabricated inductor is formed of a planar spiral formed of a continuous conductive trace extending between bonding pads that is deposited as a layer of the RF IC chip substrate, the IC chip substrate further comprises a ground plane spaced from said planar spiral, and said continuous conductive trace extending between the bonding pads is deposited over an exposed surface of a suspended platform of the IC chip substrate formed by micromachining substrate material between the exposed surface of the suspended platform and the ground plane away, to thereby reduce parasitic capacitances between adjacent turns of the trace through the IC chip substrate to the ground plane.

8. The implantable medical device of claim 7, wherein the spiral trace and bonding pads consist of a high conductivity conductor selected from the group consisting of gold, copper and aluminum-copper metallization to reduce trace height and width to thereby reduce parasitic capacitances between adjacent turns of the trace and through the IC chip substrate.

9. The implantable medical device of claim 1, wherein the IC chip substrate further comprises a ground plane, and the IC fabricated inductor is formed of a planar spiral formed of a continuous conductive trace extending between bonding pads that is suspended above and spaced from said ground plane formed by micromachining substrate material between the exposed surface of the suspended planar spiral and the ground plane away, to thereby reduce parasitic capacitances between adjacent turns of the trace and through the IC chip substrate to the ground plane.

10. The implantable medical device of claim 9, wherein the spiral trace and bonding pads consist of a high conductivity conductor selected from the group consisting of gold, copper and aluminum-copper metallization to reduce trace height and width to thereby reduce parasitic capacitances between adjacent turns of the trace and through the IC chip substrate.

11. The implantable medical device of claim 1, wherein:
said electronic circuitry comprises an RF module incorporating a telemetry transceiver comprising an RF module substrate, an IC chip mounted to said RF module substrate and said least one IC fabricated inductor is formed integrally with said IC chip mounted to said RF module thereby reducing the volumetric form factor of the RF module.

12. The implantable medical device of claim 11, wherein:
said RF module substrate has a predetermined RF module substrate thickness, a well formed in said RF module substrate extending from an RF module substrate surface through at least a portion of said RF module substrate thickness, and at least one module bonding pad formed on the RF module substrate surface;
said IC chip has predetermined IC chip substrate thickness, is mounted within said well of said RF module substrate thereby reducing the form factor of the RF module, and has at least one IC bonding pad formed on an exposed IC chip surface; and
a conductor extending between said module bonding pad and said IC bonding pad.

13. The implantable medical device of any of the claims 1–12, wherein said notch filter further comprises at least one discrete capacitor mounted to the exposed surface of said IC chip.

14. An implantable medical device operable to perform a therapeutic and/or monitoring function in a living body while exposed to sources of electromagnetic interference (EMI) comprising:
a housing having a housing side wall and inner and outer wall surfaces of a predetermined contour enclosing a hermetically sealed chamber;
a battery enclosed within said hermetically sealed chamber;
at least one sense electrode located outside said housing adapted to be located in relation to body tissue to detect electrical signals of the body tissue;
sense amplifier circuitry enclosed within said hermetically sealed chamber powered by the battery and coupled to said sense electrode, the sense amplifier circuitry comprising a plurality of discrete components and at least one integrated circuit IC chip having an IC chip substrate and mounted to a circuit board dimensioned to fit within said hermetically sealed chamber along with said battery, said sense amplifier circuitry comprising at least one notch filter that blocks EMI signal frequencies received from the sense electrode and passes signal frequencies of interest, the notch filter formed of at least one IC fabricated inductor formed integrally with said IC chip.

15. The implantable medical device of claim 14, wherein the IC fabricated inductor comprises a planar spiral formed of a continuous, conductive, spiral trace extending between bonding pads that is deposited as a layer of the IC chip substrate, the spiral trace having turning points that are angled at less than 90° to reduce parasitic capacitance between adjacent turning points of the spiral trace.

16. The implantable medical device of claim 15, wherein the spiral trace and bonding pads consist of a high conductivity conductor selected from the group consisting of gold, copper and aluminum-copper metallization to reduce trace height and width to thereby reduce parasitic capacitances between adjacent turns of the trace and through the IC chip substrate.

17. The implantable medical device of claim 16, wherein the IC chip substrate further comprises a ground plane spaced from said planar spiral, and said continuous conductive trace extending between the bonding pads is deposited over an exposed surface of a suspended platform of the IC chip substrate formed by micromachining substrate material between the exposed surface of the suspended platform and the ground plane away, to thereby reduce parasitic capacitances between adjacent turns of the trace through the IC chip substrate to the ground plane.

18. The implantable medical device of claim 14, wherein the IC fabricated inductor comprises a planar spiral formed of a continuous, conductive, spiral trace extending between bonding pads that is deposited as a layer of the IC chip substrate, the spiral trace and bonding pads consist of a high conductivity conductor selected from the group consisting of gold, copper and aluminum-copper metallization to reduce trace height and width to thereby reduce parasitic capacitances between adjacent turns of the trace and through the IC chip substrate to the ground plane.

19. The implantable medical device of claim 18, wherein the spiral trace and bonding pads consist of a high conductivity conductor selected from the group consisting of gold, copper and aluminum-copper metallization to reduce trace height and width to thereby reduce parasitic capacitances between adjacent turns of the trace and through the IC chip substrate.

20. The implantable medical device of claim 14, wherein the IC fabricated inductor is formed of a planar spiral formed of a continuous conductive trace extending between bonding pads that is deposited as a layer of the RF IC chip substrate, the IC chip substrate further comprises a ground plane spaced from said planar spiral, and said continuous conductive trace extending between the bonding pads is deposited over an exposed surface of a suspended plafform of the IC chip substrate formed by micromachining substrate material between the exposed surface of the suspended platform and the ground plane away, to thereby reduce parasitic capacitances between adjacent turns of the trace through the IC chip substrate to the ground plane.

21. The implantable medical device of claim 20, wherein the spiral trace and bonding pads consist of a high conductivity conductor selected from the group consisting of gold, copper and aluminum-copper metallization to reduce trace height and width to thereby reduce parasitic capacitances between adjacent turns of the trace and through the IC chip substrate.

22. The implantable medical device of claim 14, wherein the IC chip substrate further comprises a ground plane, and the IC fabricated inductor is formed of a planar spiral formed of a continuous conductive trace extending between bonding pads that is suspended above and spaced from said ground plane formed by micromachining substrate material between the exposed surface of the suspended planar spiral and the ground plane away, to thereby reduce parasitic capacitances between adjacent turns of the trace and through the IC chip substrate to the ground plane.

23. The implantable medical device of claim 22, wherein the spiral trace and bonding pads consist of a high conductivity conductor selected from the group consisting of gold, copper and aluminum-copper metallization to reduce trace height and width to thereby reduce parasitic capacitances between adjacent turns of the trace and through the IC chip substrate.

24. An implantable medical device operable to perform a therapeutic and/or monitoring function in a living body while exposed to sources of electromagnetic interference (EMI) comprising:

a housing having a housing side wall and inner and outer wall surfaces of a predetermined contour enclosing a hermetically sealed chamber;

a battery enclosed within said hermetically sealed chamber;

at least physiologic sensor located outside said housing adapted to be located in relation to body tissue to detect a physiologic body parameter;

physiologic signal processing circuitry enclosed within said hermetically sealed chamber powered by the battery and coupled to said physiologic sensor, the physiologic signal processing circuitry comprising a plurality of discrete components and at least one integrated circuit IC chip having an IC chip substrate and mounted to a circuit board dimensioned to fit within said hermetically sealed chamber along with said battery, said electronic circuitry comprising at least one notch filter that blocks predetermined EMI signal frequencies and passes other signal frequencies received from the physiologic sensor, the notch filter formed of at least one IC fabricated inductor formed integrally with said IC chip.

25. The implantable medical device of claim 24, wherein the IC fabricated inductor comprises a planar spiral formed of a continuous, conductive, spiral trace extending between bonding pads that is deposited as a layer of the IC chip substrate, the spiral trace having turning points that are angled at less than 90° to reduce parasitic capacitance between adjacent turning points of the spiral trace.

26. The implantable medical device of claim 25, wherein the spiral trace and bonding pads consist of a high conductivity conductor selected from the group consisting of gold, copper and aluminum-copper metallization to reduce trace height and width to thereby reduce parasitic capacitances between adjacent turns of the trace and through the IC chip substrate.

27. The implantable medical device of claim 26, wherein the IC chip substrate further comprises a ground plane spaced from said planar spiral, and said continuous conductive trace extending between the bonding pads is deposited over an exposed surface of a suspended platform of the IC chip substrate formed by micromachining substrate material between the exposed surface of the suspended platform and the ground plane away, to thereby reduce parasitic capacitances between adjacent turns of the trace through the IC chip substrate to the ground plane.

28. The implantable medical device of claim 24, wherein the IC fabricated inductor comprises a planar spiral formed of a continuous, conductive, spiral trace extending between bonding pads that is deposited as a layer of the IC chip substrate, the spiral trace and bonding pads consist of a high conductivity conductor selected from the group consisting of gold, copper and aluminum-copper metallization to reduce trace height and width to thereby reduce parasitic capacitances between adjacent turns of the trace and through the IC chip substrate to the ground plane.

29. The implantable medical device of claim 28, wherein the spiral trace and bonding pads consist of a high conductivity conductor selected from the group consisting of gold, copper and aluminum-copper metallization to reduce trace height and width to thereby reduce parasitic capacitances between adjacent turns of the trace and through the IC chip substrate.

30. The implantable medical device of claim 24, wherein the IC fabricated inductor is formed of a planar spiral formed of a continuous conductive trace extending between bonding pads that is deposited as a layer of the RF IC chip substrate, the IC chip substrate further comprises a ground plane spaced from said planar spiral, and said continuous conductive trace extending between the bonding pads is deposited over an exposed surface of a suspended platform of the IC chip substrate formed by micromachining substrate material between the exposed surface of the suspended platform and the ground plane away, to thereby reduce parasitic capacitances between adjacent turns of the trace through the IC chip substrate to the ground plane.

31. The implantable medical device of claim 30, wherein the spiral trace and bonding pads consist of a high conductivity conductor selected from the group consisting of gold, copper and aluminum-copper metallization to reduce trace height and width to thereby reduce parasitic capacitances between adjacent turns of the trace and through the IC chip substrate.

32. The implantable medical device of claim 24, wherein the IC chip substrate further comprises a ground plane, and the IC fabricated inductor is formed of a planar spiral formed of a continuous conductive trace extending between bonding pads that is suspended above and spaced from said ground plane formed by micromachining substrate material between the exposed surface of the suspended planar spiral and the ground plane away, to thereby reduce parasitic capacitances between adjacent turns of the trace and through the IC chip substrate to the ground plane.

33. The implantable medical device of claim 32, wherein the spiral trace and bonding pads consist of a high conductivity conductor selected from the group consisting of gold, copper and aluminum-copper metallization to reduce trace height and width to thereby reduce parasitic capacitances between adjacent turns of the trace and through the IC chip substrate.

34. An implantable medical device operable to perform a therapeutic and/or monitoring function in a living body while exposed to sources of electromagnetic interference (EMI) comprising:

a housing having a housing side wall and inner and outer wall surfaces of a predetermined contour enclosing a hermetically sealed chamber;

a battery enclosed within said hermetically sealed chamber;

electronic circuitry enclosed within said hermetically sealed chamber powered by the battery comprising a plurality of discrete components and at least one integrated circuit IC chip having an IC chip substrate and mounted to a circuit board dimensioned to fit within said hermetically sealed chamber along with said battery, said electronic circuitry comprising at least one notch filter having an input and output that blocks passage of predetermined EMI signal frequencies and passes other signal frequencies from the input to the output, the notch filter formed of at least one IC fabricated microelectromechanical filter element formed integrally with said IC chip.

35. The implantable medical device of claim 34, wherein the electronic circuitry further includes an amplifier coupled to the microelectromechanical filter and a demodulator coupled to the amplifier; and wherein the microelectromechanical filter, the amplifier and the demodulator are fabricated on a common IC die.

36. The implantable medical device of claim 34, wherein:

said implantable medical device further comprises at least one sense electrode located outside said housing adapted to be located in relation to body tissue to conduct electrical signals of the body tissue having a predetermined frequency bandwidth to said electronic circuitry;

the electronic circuitry comprises a sense amplifier circuit for amplifying and processing the electrical signals of the body tissue; and the microelectromechanical filter is coupled electrically between the sense electrode and a stage of the sense amplifier circuit and is tuned to pass the electrical signals of body tissue and to not pass EMI signal frequencies.

37. The implantable medical device of claim 34, wherein:

said implantable medical device further comprises a telemetry antenna and a telemetry transceiver coupled to the telemetry antenna enabling telemetry transmissions with other medical devices at a predetermined telemetry carrier frequency and data encoding bandwidth; and the microelectromechanical filter is coupled electrically between the telemetry antenna and telemetry transceiver and tuned to pass the telemetry carrier frequency and data encoding frequencies and to not pass predetermined EMI signal frequencies.

38. The implantable medical device of claim 34, wherein:

said implantable medical device further comprises at least one physiologic sensor located outside said housing adapted to be located in relation to body tissue to measure a physiologic parameter of the body and provide a physiologic signal having a predetermined frequency bandwidth to said electronic circuitry;

the electronic circuitry comprises a physiologic signal processor circuit for amplifying and processing the physiologic signals of the body tissue having a predetermined frequency bandwidth; and the microelectromechanical filter is coupled electrically between the physiologic sensor and a stage of the physiologic signal processor circuit sense amplifier circuit and tuned to pass the physiologic signals of body tissue and to block predetermined EMI signal frequencies.

* * * * *